United States Patent [19]

Langenbach, Jr.

[11] Patent Number: 4,593,694
[45] Date of Patent: Jun. 10, 1986

[54] TWEEZERS

[75] Inventor: George F. Langenbach, Jr., 9127 Pardee Spur, Crestwood, Mo. 63126

[73] Assignee: George Langenbach, Crestwood, Mo.

[21] Appl. No.: 519,061

[22] Filed: Aug. 1, 1983

[51] Int. Cl.$^4$ .......................... A61B 17/30; B25B 9/02
[52] U.S. Cl. .......................................128/354; 81/418; 128/355; 294/99.2
[58] Field of Search ................................ 128/354–355; 81/43, 120, 186, 418; 294/99.1, 99 R, 99.2

[56] References Cited

U.S. PATENT DOCUMENTS

| | | | |
|---|---|---|---|
| 220,390 | 10/1879 | Koska | 128/354 |
| 449,408 | 3/1891 | Evans | 81/43 |
| 809,244 | 1/1906 | Blomquist | 294/99.2 |
| 979,697 | 12/1910 | Prankard, Jr. | |
| 1,701,995 | 2/1929 | Anderson | 128/355 |
| 2,089,177 | 8/1937 | Beldne | 81/418 |
| 2,199,685 | 5/1940 | Wood | 294/99.2 |
| 2,887,110 | 5/1959 | Roeschmann | 81/418 |
| 3,664,346 | 5/1972 | Dunn | 128/355 |
| 4,213,460 | 7/1980 | Weiner | 128/355 |
| 4,409,184 | 10/1983 | Giroir | 128/354 |

*Primary Examiner*—Stephen C. Pellegrino
*Assistant Examiner*—Gene B. Kartchner
*Attorney, Agent, or Firm*—Senniger, Powers, Leavitt and Roedel

[57] ABSTRACT

Tweezers for withdrawing hair from the skin comprising a pair of legs having flat opposing inner surfaces and outer surfaces which flare outwardly at their free ends to form broad flat feet for contacting the skin and for gripping a hair near its base between the opposing inner surfaces.

1 Claim, 3 Drawing Figures

TWEEZERS

BACKGROUND OF THE INVENTION

This invention relates generally to tweezers, and more particularly to tweezers for withdrawing hair from the skin.

Tweezers are commonly used to remove unwanted hairs from the skin. However, when a hair cannot be seen without the aid of a mirror or the like, such as when the hair is at the side of the head, on the back or in the ear, it can be difficult for a person to remove his own unwanted hair without causing injury to himself. This is due to the fact that the ends of tweezers are normally sharp and thereby results in the gouging or pinching of the skin. Reference may be made to U.S. Pat. No. 979,697 which shows a device designed to prevent the aforementioned injuries.

SUMMARY OF THE INVENTION

Among the several objects of this invention may be noted the provision of an improved tweezer which is designed not to gouge or pinch the skin; and the provision of such tweezers which is simple and economical in construction.

Generally, tweezers of this invention are used for withdrawing hair from the skin and comprise a pair of legs having flat opposing inner surfaces and outer surfaces which flare outwardly at their free ends to form broad flat feet for contacting the skin and for gripping a hair near its base between the opposing inner surfaces.

Other objects and features will be in part apparent and in part pointed out hereinafter.

BRIEF DESCRIPTION OF THE DRAWINGS

Corresponding reference characters indicate corresponding parts throughout the several views of the drawings.

DESCRIPTION OF A PREFERRED EMBODIMENT

Figure 1:
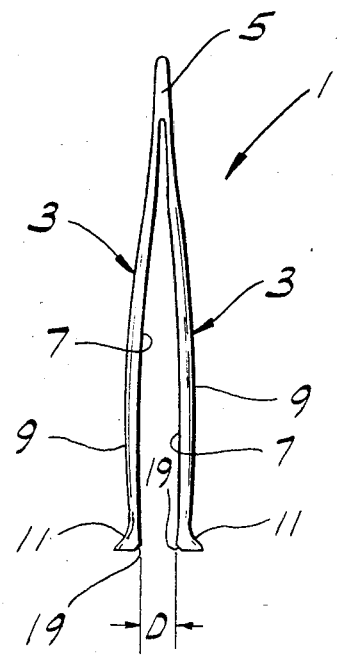
FIG. 1 is a side elevation of tweezers of this invention.

Referring to FIG. 1, tweezers of this invention is indicated in its entirety at 1. It is shown having a pair of legs 3 joined at one of their ends and forming a head 5. The legs 3 have flat opposing inner surfaces 7 and outer surfaces 9 which flare outwardly at their free ends 11 to form broad flat feet 11. The distance D between the feet is relatively small for reasons which will be apparent later.

Figure 2:
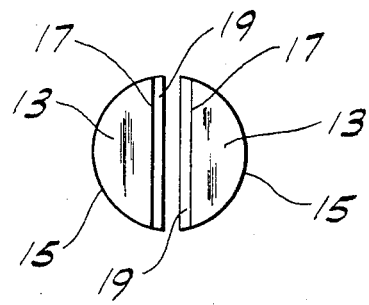
FIG. 2 is a bottom plan or FIG. 1.

As seen in FIG. 2, the bottom surfaces 13 of the feet 11 are generally semicircular in shape, the arc 15 of the semicircle defining the outer edge of each foot and the diameter or chord line 17 of the semicircle defining the inside edge of each foot. The inside surfaces of the feet are slightly relieved at the opposing bottom edges 19 thereof. When the feet are squeezed together the bottom of the feet generally form a circle with a slot through the center thereof.

Figure 3:
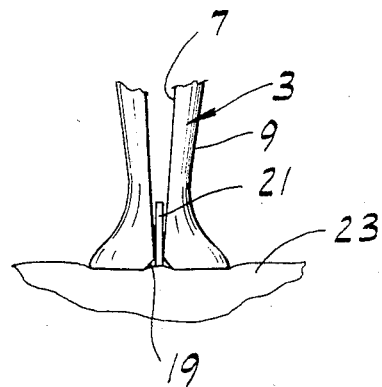
FIG. 3 is an enlarged fragmentary view of the feet portion of the tweezers shown grasping a hair.

As shown in FIG. 3, in order to remove an unwanted hair 21 from the skin 23 the feet 11 are brought in contact with the skin's surface and positioned straddling the hair. Since the bottom surfaces of feet 11 are flat, as shown in the drawings, not pointed, and have no sharp opposing edges, the chances of a person gouging or pinching himself are greatly reduced. Once the feet 11 are positioned, they are then squeezed together by pressing the legs 3 inwardly. This allows the feet 11 to grip the hair near its base between the opposing inner surfaces 7. Since the distance D between the feet is relatively small and the otherwise sharp opposing bottom edges are relieved at 19, there is little if any chance of pinching the skin.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. Tweezers for withdrawing hair from the skin comprising a pair of legs, said legs terminating in free ends having flat opposing inner surfaces and outer surfaces which flare outwardly at said free ends to form broad flat feet for contacting the skin and for directly gripping a hair near the base thereof between the opposing inner surfaces of said feet, the bottom surfaces of said feet being generally semicircular in shape, the arc of said semicircle defining the outer edge of each foot and the chord line of said semicircle defining the inner edge of each foot, so that when the feet are squeezed together the bottom of the feet generally form a circle, the inside surfaces of the feet being slightly relieved at the opposing bottom edges thereof so that the feet may be squeezed together directly to grip a hair without pinching the flesh.

* * * * *